United States Patent
Brodwick

(10) Patent No.: US 11,723,851 B2
(45) Date of Patent: Aug. 15, 2023

(54) PERSONAL CARE DEODORANT PRODUCT VOID OF ENDOCRINE DISRUPTING CHEMICALS

(71) Applicant: thinkOperations, LLC, Austin, TX (US)

(72) Inventor: Kevin Brodwick, Austin, TX (US)

(73) Assignee: thinkOperations, LLC, Austin, TX (US)

( * ) Notice: Subject to any disclaimer, the term of this patent is extended or adjusted under 35 U.S.C. 154(b) by 19 days.

(21) Appl. No.: 16/056,759

(22) Filed: Aug. 7, 2018

(65) Prior Publication Data

US 2019/0046424 A1 Feb. 14, 2019

Related U.S. Application Data

(60) Provisional application No. 62/542,445, filed on Aug. 8, 2017.

(51) Int. Cl.

| | |
|---|---|
| *A61Q 15/00* | (2006.01) |
| *A61K 8/19* | (2006.01) |
| *A61K 8/36* | (2006.01) |
| *A61K 8/92* | (2006.01) |
| *A61K 8/67* | (2006.01) |
| *A61K 8/9794* | (2017.01) |
| *A61K 8/73* | (2006.01) |
| *A61K 8/37* | (2006.01) |
| *A61K 8/9789* | (2017.01) |

(52) U.S. Cl.
CPC ............... *A61K 8/361* (2013.01); *A61K 8/19* (2013.01); *A61K 8/375* (2013.01); *A61K 8/671* (2013.01); *A61K 8/731* (2013.01); *A61K 8/735* (2013.01); *A61K 8/922* (2013.01); *A61K 8/9789* (2017.08); *A61K 8/9794* (2017.08); *A61Q 15/00* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 2006/0165623 A1* | 7/2006 | Workman | A61K 8/9711 424/65 |
| 2014/0050672 A1* | 2/2014 | Rao | A61K 31/23 424/43 |
| 2016/0095814 A1* | 4/2016 | Florence | A61K 8/342 424/60 |

OTHER PUBLICATIONS

Cosmetics Challenge: Six Strategies for Scientific Skincare, Part 2 of 2 (Practical Dermatology)(Aug. 2010).*
Naveed (J. Pharm. Sci. & Res. vol. 6(1), 2014, 338-341).*

* cited by examiner

*Primary Examiner* — Patricia Duffy
*Assistant Examiner* — Garen Gotfredson
(74) *Attorney, Agent, or Firm* — Lowenstein Sandler LLP

(57) ABSTRACT

A personal care deodorant and/or antiperspirant product substantially void of any endocrine disrupting chemicals, and a method of making the same. Embodiments of the deodorant include one or more of the following: a skin conditioning agent, an emollient, a nonaqueous viscosity increasing agent, a surfactant/emulsifying agent, an absorbent, a soothing agent, a deodorant agent, a viscosity-controlling agent, and a scent.

8 Claims, No Drawings

PERSONAL CARE DEODORANT PRODUCT VOID OF ENDOCRINE DISRUPTING CHEMICALS

The present application claims priority from U.S. Provisional Patent Application No. 62/542,445, filed Aug. 8, 2017, which is hereby incorporated by reference.

TECHNICAL FIELD OF THE INVENTION

The technical field of embodiments of the present invention is personal care products, specifically personal care products that are substantially free of endocrine disrupting chemicals.

BACKGROUND OF THE INVENTION

There is increasing evidence that certain synthetic and natural chemicals, called endocrine disruptors, may act as antagonists or antagonists to estrogens or androgens and may interfere in multiple ways with the action of thyroid hormones. For example, endocrine disruptors can mimic or block chemicals naturally found in the body, thereby altering the body's ability to produce hormones, interfering with the ways hormones travel through the body, and altering the concentration of hormones reaching hormone receptors. Although relatively few chemicals have been examined for their endocrine disruptive effect, those chemicals that have shown such an effect are increasingly found in common food, plastic, and personal care products.

Endocrine disruptors include chemicals such as, for example, polychlorinated biphenyls (PCBs), dioxins and furans. These chemicals are found environmentally in insecticides, herbicides, fumigants, and fungicides that are used in agriculture as well as in the home. Other endocrine disruptors are found in common chemicals such as detergents, dental amalgams and resins that coat the inside of tin cans. In addition, research has found that, because the polymerization process used to make plastics is not complete, unpolymerized monomers with estrogenic activity can migrate out of plastics resulting in deleterious estrogenic, carcinogenic or toxic effects in humans and other species.

By way of example, di(2-ethylhexyl) phthalate (DEHP) is a plasticizer that is a colorless liquid with almost no odor. DEHP is commonly used in producing polyvinyl chloride (PVC) plastic products like toys, vinyl upholstery, shower curtains, adhesives, and coatings. PVC plastic may contain up to 40% DEHP. DEHP, an estrogen-mimicking chemical, has been found to leach from these plastics, thereby creating problems with the materials in contact with the plastic. For example, DEHP has been found to leach from intravenous bags and tubing into the blood and medications being administered to patients. Exposure to DEHP through intravenous bags and tubing presents a health risk that could be avoided through the use of a plastic material that does not contain endocrine disruptive chemicals.

Similarly, bisphenol A is a monomer used to synthesize a number of plastics, such as polycarbonates, epoxy, phenoxy and polysulfone polymers, and is released in significant amounts when these plastics are exposed to water, particularly when heated. Bisphenol A has been shown to possess deleterious estrogenic activity. Nevertheless, plastics manufactured with bisphenol A, such as polycarbonate, are commonly used for food and beverage containers, baby bottles, baby toys, microwaveable containers and medical items.

There are concerns regarding the use of endocrine disrupting organic substances in nearly all UV screening chemicals used in sunscreens. The association between the exposure and bioaccumulation of endocrine disruptor chemicals (EDCs) and their adverse effects on human and wild life populations has raised concern worldwide. Some examples of the effects of EDCs are: decreased reproductive success and feminization of males in several wildlife species; increased hypospadias along with reductions in sperm counts in men; increase in the incidence of human breast and prostate cancers; and endometriosis. Because these chemicals are ubiquitous, highly lipophilic, and often chlorinated, this ensures their persistent presence in the environment resulting in their bioaccumulation in the food chain.

Research also shows that some compounds used in personal care products, such as deodorant, are absorbed and stored in fat cells, which are prevalent in the underarm area. Underarm tissue also contains hormone receptors, which could react to some of those same deodorant ingredients. Chemicals placed on the skin can enter the bloodstream without being metabolized. Blood tests in recent research show that many of the substances commonly included in deodorant products can get past the epidermis and into the body. Certain compounds in antiperspirant and deodorant could cause or contribute to developmental or reproductive issues, as well as cancer. There are at least five deodorant ingredients of concern, in particular: parabens, aluminum, triclosan, phthalates, and fragrances.

There are many different parabens. Parabens are used as preservatives in deodorant and other personal care products. Research suggests some parabens may interfere with the way your body produces and regulates estrogen and other hormones. For example, the breast includes estrogen-sensitive tissue. A concern of placing parabens close to this tissue every day is that the parabens may promote the growth of cancer cells, and in both men and women. Research has shown that mixing different parabens can strengthen their estrogenic effects. Existing evidence suggests that long-term, low-dose mixtures of environmental chemicals—including parabens—could cause cancer.

Typically found only in antiperspirants, aluminum can cause gene instability in breast tissue, research shows. This instability can cause changes than may promote the growth of tumors or cancer cells. Over 50% of breast cancers start in the upper outer quadrant of the breast local to the underarm region. Breast cancer incidence tends to align with use of products that contain aluminum. The situation is made worse by applying a product containing aluminum to an area that is frequently shaved had may have broken skin.

Cosmetic manufacturers add triclosan to many products in order to prevent bacterial contamination, and to kill bacteria on the surface of the skin, as in anti-acne products, some deodorants and antiperspirants, and in sanitizing hand soaps. Triclosan is so common that 75% of Americans have detectable levels of the stuff in their urine.

Some animal studies have linked triclosan to unusual hormone activity. More research suggests triclosan could mess with your microbiome or the day-to-day operations of your genes. There is evidence from amphibians and fish is that triclosan impairs thyroid function, which is crucial for brain development. Blood tests show triclosan is at the high end when it comes to chemicals found in people's bodies.

Phthalates help deodorant and other cosmetics—such as fragrance—stick to your skin. They also appear to disrupt "androgen function," or the way your body produces and uses the hormone testosterone. Testosterone, found in both men and women, plays a role in energy and muscle maintenance. Phthalates could impair reproductive ability in men. Phthalates could impact fetal development in pregnant women. Research has also linked phthalates to lower IQs and higher rates of asthma. Phthalates are typically present in any product with a fragrance that lingers after it's been used or applied; phthalates are partly what makes smells stick. That means that everything from body wash to shampoo to lotion to hairspray to soap.

Almost every scented product has fragrance or perfume listed among its ingredients. It is difficult to know what specific chemicals are included in the terms "fragrance" or "perfume" because scents are protected under trade law. The terms could refer to phthalates, or they could be substances that cause allergies or skin irritation. Even smelling scented products on other people can cause an allergic reaction.

SUMMARY OF THE INVENTION

Embodiments of the present invention are directed to a personal care deodorant and/or antiperspirant product substantially void of any endocrine disrupting chemicals, and a method of making the same. Embodiments of the deodorant include one or more of the following: a skin conditioning agent, an emollient, a nonaqueous viscosity increasing agent, a surfactant/emulsifying agent, an absorbent, a soothing agent, a deodorant agent, a viscosity-controlling agent, and a scent.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF EMBODIMENTS

Embodiments of the present invention are directed to personal care deodorant and anti-perspirant products that are void of and do not contain any endocrine disrupting chemicals, and a method of making the same. An embodiment of the personal care deodorant product can be used as an underarm deodorant to reduce/prevent body odor. An embodiment of the personal care anti-perspirant product can used to prevent perspiration, typically under the arm, thereby reducing/preventing the body odor resulting from underarm perspiration. Embodiments of the personal care deodorant/anti-perspirant product can be used as a substitute for traditional underarm deodorants that include chemicals that are known to have endocrine disrupting effects or are suspected of having endocrine disruptive effects.

The term "deodorant" will be used herein to refer collectively to personal care deodorant and antiperspirant products in accordance with embodiments of the present invention.

Embodiments of the deodorant include one or more of the following: a skin conditioning agent, an emollient, a nonaqueous viscosity increasing agent, an aqueous viscosity-increasing agent, a surfactant/emulsifying agent, an absorbent, a soothing agent, a deodorant agent, a viscosity-controlling agent, and a scent.

The skin conditioning agent is used to increase water content on surface of the skin. The skin conditioning agent can include caprylic/capric triglyceride, aloe vera, allantonin, rose hip oil, beta glucan, bamboo extract, carrot cells, glycoproteins, cucumber fruit extract, grape seed extract, hyaluronic acid, mulberry root, rosemary, sage, vitamin A, and White tea extract. Caprylic/capric triglyceride, aloe vera, allantonin, rose hip oil, beta glucan, bamboo extract, carrot cells, glycoproteins, cucumber fruit extract, grape seed extract, hyaluronic acid, mulberry root, rosemary, sage, vitamin A, and White tea extract are not known to have any endocrine disrupting effects.

The emollient is used to soften the skin and increase the moisture on the skin by reducing evaporation. The emollient can include oil from *Cocos nucifera* (coconut oil), hemp seed oil, jojoba oil, green tea, keratin protein, oat amino acids, and sunflower oil. *Cocos nucifera*, hemp seed oil, jojoba oil, green tea, keratin protein, oat amino acids, and sunflower oil are not known to have any endocrine disrupting effects.

The nonaqueous viscosity-increasing agent is used to thicken of the liquid (oil) portion of cosmetic formulations. The nonaqueous viscosity-increasing agent can include wax from *Euphorbia cerifera* (Candelilla), polyethylenes, trihydroxystearin, organoclays, fumed silica. *Euphorbia cerifera* (Candelilla) wax, polyethylenes, trihydroxystearin, organoclays, fumed silica are not known to have any endocrine disrupting effects.

The aqueous viscosity-increasing agent is used to thicken of the liquid (water) portion of cosmetic formulations. The aqueous viscosity-increasing agent can include cellulose gum, guar gum, xanthan gum, hydroxyethylcellulose, methylcellulose, polyethylene glycols, and clays. Cellulose gum, guar gum, xanthan gum, hydroxyethylcellulose, methylcellulose, polyethylene glycols, clays are not known to have any endocrine disrupting effects.

The surfactant/emulsifying agent is used to lower the surface tension between two liquids or a liquid and a solid. The surfactant/emulsifying agent can include wax from Cera alba (beeswax), sulfate, sulfonate, phosphate, and carboxylates, ammonium lauryl sulfate, sodium lauryl sulfate (SLS), sodium dodecyl sulfate (SDS), alkyl-ether sulfates, sodium laureth sulfate, sodium lauryl ether sulfate (SLES), sodium myreth sulfate, sodium stearate, sodium lauroyl sarcosinate, cocamidopropyl betaine, Lauryl glucoside, Glyceryl laurate, Cocamide MEA, and cocamide DEA. Cera alba wax (beeswax), sulfate, sulfonate, phosphate, and carboxylates, ammonium lauryl sulfate, sodium lauryl sulfate (SLS), sodium dodecyl sulfate (SDS), alkyl-ether sulfates, sodium laureth sulfate, sodium lauryl ether sulfate (SLES), sodium myreth sulfate, sodium stearate, sodium lauroyl sarcosinate, cocamidopropyl betaine, Lauryl glucoside, Glyceryl laurate, Cocamide MEA, and cocamide DEA are not known to have any endocrine disrupting effects.

The absorbent is used to absorb perspiration that can cause body odor, particularly in the underarm area. The absorbent can include starch from *Zea mays* (corn starch), arrowroot powder, sodium stearate, sodium bicarbonate, charcoal, and dextrin. *Zea mays* (corn starch), arrowroot powder, sodium stearate, sodium bicarbonate, charcoal, and dextrin are not known to have any endocrine disrupting effects.

The soothing agent is used to provide care to irritated or stressed skin or to reduce the potential for irritated or stressed skin. The soothing agent can include *Maranta arundinacea* (arrowroot) powder, caprylic/capric triglyceride, aloe vera, allantonin, rose hip oil, beta glucan, bamboo extract, carrot cells, glycoproteins, cucumber fruit extract, grape seed extract, hyaluronic acid, mulberry root, rosemary, sage, vitamin A, and White tea extract. *Maranta arundinacea* (arrowroot) powder, caprylic/capric triglyceride, aloe vera, allantonin, rose hip oil, beta glucan, bamboo extract, carrot cells, glycoproteins, cucumber fruit extract, grape seed extract, hyaluronic acid, mulberry root, rosemary, sage, vitamin A, and White tea extract are not known to have any endocrine disrupting effects.

The deodorant agent is used to reduce or eliminate body odor in and around the area where the deodorant is applied. The deodorant agent can include sodium bicarbonate and/or sodium stearate. Sodium bicarbonate and sodium steari not known to have any endocrine disrupting effects.

The viscosity-controlling agent is used to control the thickness of aqueous and nonaqueous cosmetic formulation. The viscosity-controlling agent can include *Butyrospermum parkii* (Shea) butter, cera alba wax (beeswax), sulfate, sulfonate, phosphate, and carbo, xylates, ammonium lauryl sulfate, sodium lauryl sulfate (sodium dodecyl sulfate, SLS, or SDS, alkyl-ether sulfates sodium laureth sulfate (sodium lauryl ether sulfate or SLES), and sodium myreth sulfate, sodium stearate, sodium lauroyl sarcosinate, cocamidopropyl betaine, Lauryl glucoside, Glyceryl laurate, Cocamide MEA, and cocamide DEA. *Butyrospermum parkii* (Shea) butter, cera alba wax (beeswax), sulfate, sulfonate, phosphate, and carbo, xylates, ammonium lauryl sulfate, sodium lauryl sulfate (sodium dodecyl sulfate, SLS, or SDS, alkyl-ether sulfates sodium laureth sulfate (sodium lauryl ether sulfate or SLES), and sodium myreth sulfate, sodium stearate, sodium lauroyl sarcosinate, cocamidopropyl betaine, Lauryl glucoside, Glyceryl laurate, Cocamide MEA, and cocamide DEA are not known to have any endocrine disrupting effects.

Scent is used to give the product a pleasing smell and to mask any residual body odor that is not entirely eliminated by the deodorant agent. Scent can include currant, *Citrus paradisi* (grapefruit), Essential oils, fruit extract, fruit oil, flower oil, flower powder, flower extract. Currant, *Citrus paradisi*, Essential oils, fruit extract, fruit oil, flower oil, flower powder, and flower extract are not known to have any endocrine disrupting effects.

Embodiments of the present invention do not include and are substantially void of parabens, aluminum, triclosan, phthalates, di(2-ethylhexyl) phthalate (DEHP), bisphenol A (BPA).

Although the present invention and its advantages have been described in detail, it should be understood that various changes, substitutions and alterations can be made herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A personal care deodorant product substantially void of any endocrine disrupting chemicals, the personal care deodorant product consisting of:
   a skin conditioning agent substantially void of any endocrine disrupting chemicals in which the skin conditioning agent is selected from a group consisting of: caprylic/capric triglyceride, aloe vera, allantoin, rose hip oil, beta glucan, bamboo extract, carrot cells, glycoproteins, cucumber fruit extract, grape seed extract, hyaluronic acid, mulberry root, rosemary, sage, vitamin A, and white tea extract;
   an emollient substantially void of any endocrine disrupting chemicals in which the emollient is selected from a group consisting of: *Cocos nucifera* (coconut) oil, hemp seed oil, jojoba oil, green tea, keratin protein, oat amino acids, and sunflower oil;
   a nonaqueous viscosity increasing agent substantially void of any endocrine disrupting chemicals in which the nonaqueous viscosity-increasing agent is selected from group consisting of: *Euphorbia cerifera* (Candelilla) wax, polyethylenes, trihydroxystearin, organoclays, and fumed silica;
   a surfactant/emulsifying agent substantially void of any endocrine disrupting chemicals in which the surfactant/emulsifying agent is selected from the group consisting of: cera alba wax (beeswax), sulfate, sulfonate, phosphate, carboxylates, ammonium lauryl sulfate, sodium lauryl sulfate (SLS), sodium dodecyl sulfate (SDS), alkyl-ether sulfates, sodium laureth sulfate, sodium lauryl ether sulfate (SLES), sodium myreth sulfate, sodium stearate, sodium lauroyl sarcosinate, cocamidopropyl betaine, lauryl glucoside, glyceryl laurate, cocamide MEA, and cocamide DEA;
   an absorbent substantially void of any endocrine disrupting chemicals in which the absorbent is selected from a group consisting of: *Zea mays* (corn) starch, arrowroot powder, sodium stearate, sodium bicarbonate, charcoal, and dextrin;
   a deodorant agent substantially void of any endocrine disrupting chemicals in which the deodorant agent is selected from a group consisting of: sodium bicarbonate and sodium stearate;
   a viscosity-controlling agent substantially void of any endocrine disrupting chemicals in which the viscosity-controlling agent is selected from a group consisting of: *Butyrospermum parkii* (Shea) butter, cera alba wax (beeswax), sulfate, sulfonate, phosphate, carboxylates, ammonium lauryl sulfate, sodium lauryl sulfate (SLS), sodium dodecyl sulfate (SDS), alkylether sulfates, sodium laureth sulfate, sodium lauryl ether sulfate (SLES), sodium myreth sulfate, sodium stearate, sodium lauryl sarcosinate, cocamidopropyl betaine, lauryl glucoside, glyceryl laurate, cocamide MEA, and cocamide DEA; and
   a scent substantially void of any endocrine disrupting chemicals in which the scent is selected from a group consisting of: currant, *Citrus paradisi* (grapefruit), Essential oils, fruit extract, fruit oil, flower oil, flower powder, and flower extract.

2. The personal care deodorant product of claim 1, wherein the personal care deodorant product does not include parabens, aluminum, triclosan, phthalates, di(2-ethylhexyl) phthalate (DEHP), and bisphenol A (BPA).

3. The personal care deodorant product of claim 1 substantially void of parabens.

4. The personal care deodorant product of claim 1 substantially void of aluminum.

5. The personal care deodorant product of claim 1 substantially void of triclosan.

6. The personal care deodorant product of claim 1 substantially void of phthalates.

7. The personal care deodorant product of claim 1 substantially void of di(2-ethylhexyl) phthalate (DEHP).

8. The personal care deodorant product of claim 1 substantially void of bisphenol A (BPA).

\* \* \* \* \*